(12) United States Patent
Fogg

(10) Patent No.: US 10,278,596 B2
(45) Date of Patent: May 7, 2019

(54) SYSTEM AND METHOD FOR VECTOR MODELING EKG SIGNALS

(71) Applicant: Harold T. Fogg, Aurora, CO (US)

(72) Inventor: Harold T. Fogg, Aurora, CO (US)

( * ) Notice: Subject to any disclaimer, the term of this patent is extended or adjusted under 35 U.S.C. 154(b) by 0 days.

(21) Appl. No.: 15/927,681

(22) Filed: Mar. 21, 2018

(65) Prior Publication Data

US 2018/0271384 A1      Sep. 27, 2018

Related U.S. Application Data

(60) Provisional application No. 62/474,725, filed on Mar. 22, 2017.

(51) Int. Cl.
*A61B 5/04* (2006.01)
*A61B 5/0245* (2006.01)
*G06F 17/18* (2006.01)
*G06F 17/16* (2006.01)
*A61B 5/0402* (2006.01)

(52) U.S. Cl.
CPC ........ *A61B 5/0245* (2013.01); *A61B 5/04011* (2013.01); *G06F 17/16* (2013.01); *G06F 17/18* (2013.01); *A61B 5/04021* (2013.01)

(58) Field of Classification Search
CPC .......................... A61B 5/0245; A61B 5/04021
USPC ......................................................... 600/509
See application file for complete search history.

*Primary Examiner* — Nadia A Mahmood
(74) *Attorney, Agent, or Firm* — Shifrin Patent Law; Dan Shifrin

(57) ABSTRACT

A system and method are provided for generating EKG signal vectors for EKG sensing positions, comprising receiving an EKG axis vector and generating two or more component vectors from the EKG axis vector, each component vector identified by a magnitude and direction.

32 Claims, 8 Drawing Sheets

SYSTEM AND METHOD FOR VECTOR MODELING EKG SIGNALS

RELATED APPLICATION DATA

The present application is related to and claims the benefit of commonly-owned and U.S. Provisional Application Ser. No. 62/474,725 entitled SYSTEM AND METHOD FOR VECTOR MODELING EKG SIGNALS, filed on Mar. 22, 2017, which application is incorporated herein by reference in its entirety.

The present application is also related to the following commonly-owned U.S. Pat. No. 10,067,498, entitled PHYSIOLOGICAL ELECTRICAL SIGNAL SIMULATOR; U.S. provisional application Ser. No. 15/335,763 entitled SYSTEM AND METHOD FOR MODELING ECG SIGNAL SOURCES, filed on Oct. 27, 2016, which patent and application are incorporated herein by reference in their entireties. The present invention is also related to commonly-owned U.S. Pat. No. 9,489,345, entitled SYSTEM AND METHOD FOR PROVIDING PRODUCTS AND LOCATIONS, U.S. Pat. No. 10,140,316, entitled SYSTEM AND METHOD FOR SEARCHING, WRITING, EDITING, AND PUBLISHING WAVEFORM SHAPE INFORMATION, which patents are incorporated herein by reference in their entireties; U.S. Pat. No. 10,067,498, entitled PHYSIOLOGICAL SIGNAL STIMULATOR AND SIMULATOR; U.S. Pat. No. 9,901,259, entitled SYSTEM FOR GENERATING CARDIAC WAVEFORMS, and Ser. No. 15/194,762, entitled METHOD AND SYSTEM TO ISOLATE AND DISPLAY ESTIMATED ECG WAVES and filed on Jun. 28, 2016.

TECHNICAL FIELD

The present invention relates generally to the field of cardiology and, in particular, to a system and method for modeling a heart's electrical activity.

BACKGROUND ART

Electrocardiography is a non-invasive procedure used to sense from electrodes on the skin a signal representing electrical activity of the heart and to record and display the signal. A medical professional may then analyze the resulting electrocardiogram (EKG) to detect signs of heart abnormalities. Medical professionals are trained to determine whether an EKG is normal or abnormal and through the study of many EKGs both real and simulated, they decide whether an abnormal EKG indicates disease or is simply unusual. Skilled professionals effectively predict an amazing variety of abnormalities inside the heart from analysis of data provided by non-invasive EKGs.

When an EKG is performed, it is common to place six electrodes across the patient's chest and one electrode is placed on each limb. Focusing on the limb electrodes, EKG circuitry designates each electrode as positive or negative to create three "leads," each with a view of the heart and an angle of orientation. The angles of orientation for leads I, II, and III are 0°, 60°, and 120°, respectively. Three additional, augmented leads are also created with different views of the heart and angles of orientation. The angles of orientation for leads aVL, aVR, and aVF are −30°, −150°, and 90°, respectively. Each electrode measures electrical activity within the heart and each lead is considered to represent a vector with an angle of orientation A representing an average direction and a voltage representing an amplitude. FIG. 1 illustrates the convention used to define the angles A.

Occasionally, the electrodes placed on the legs will be reversed. However, it is believed that such reversal is not often detected from an EKG chart and therefore is assumed to have no discernable effect on the EKG.

SUMMARY OF THE INVENTION

The present invention provides a system for generating EKG signal vectors for EKG sensing positions. The system comprises a processing module for receiving an EKG axis vector and generating two or more component vectors from the EKG axis vector, each component vector identified by a magnitude and direction.

More specifically, embodiments of the present invention provide a system for generating a sequence of vector component sets. The system comprises an input module for receiving a representation of a vector V; a processing module for providing xV and yV from the received vector V, such that V is represented by xV(1 ... M) and yV(1 ... M), where M is an integer greater than zero; a sequence generating module for generating a sequence of x-components, where xV equals the sum of xV(1) through xV(M), M being an integer greater than zero, and for generating a sequence of y-components, where yV equals the sum of yV(1) through yV(1); and an output module for providing sets of values for xV and yV up to a maximum number of sets of values as a function of xV, yV, and M, whereby a sequence of vector component sets is generated.

Embodiments also provide a method for generating a sequence of vector component sets. The method comprises receiving a representation of a vector V; providing xV and yV from the received vector V, such that V is represented by xV(1 ... M) and yV(1 ... M), where M is an integer greater than zero; generating a sequence of x-components, where xV equals the sum of xV1 through xV(M), and for generating a sequence of y-components, where yV equals the sum of yV1 through yV(N); and providing sets of values for xV and yV up to a maximum number of sets as a function of xV, yV, whereby a sequence of vector component sets is generated.

Embodiments of the present invention further provide a system and method for providing an electrocardiogram (EKG) axis angle (A). The system comprises an input module to receive EKG signals representing Lead 1 and Lead 2; and a processing module to provide a voltage V(0) from Lead 1 and a voltage V(90) from Lead 2, where V(0) represents a voltage at an angle of zero degrees and V(90) represents the voltage at an angle of 90 degrees in a model used to identify angular relationships between EKG leads. The processing model is configured to provide a voltage V(−90) as a function of V(0) and V(90); and to calculate the axis angle A as a function of V(90), V(−90) and V(0).

A system also provides an electrocardiogram (EKG) axis angle (A). The system comprises an input module to receive EKG signals representing Lead 1 and Lead 2; and a processing module to provide a voltage V(0) from Lead 1 and a voltage V(90) from Lead 2, where V(0) represents a voltage at an angle of zero degrees and V(90) represents the voltage at an angle of 90 degrees in a model used to identify angular relationships between EKG leads. The processing model is configured to provide a voltage V(−90) as a function of V(0) and V(90); and to calculate the axis angle A as a function of V(90), V(−90) and V(0).

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

One requirement for a model is that it provides a way of realistically relating voltages sensed at Right Arm (R), Left Arm (L), and Left Leg (F) with a corresponding electrical heart axis. Voltages R, L, and F are related to limb leads by the relations: Lead I=L−R; Lead II=F−R, and Lead III=F−L.

In common practice the voltages R, L, and F are measured with respect to a common connection on the Right Leg (RL). It is also common to calculate augmented voltages aVR, aVL, and aVF from the relations:

$$aVR=R-\tfrac{1}{2}(L+F);$$

$$aVL=L-\tfrac{1}{2}(F+R);$$

$$aVF=F-\tfrac{1}{2}(L+R);$$

Since voltages for leads I, II, and III are all differences between two related voltages, we can set R=0 without changing Lead Voltages.

With R=0, the lead relations are simplified to:

$$I=L;$$

$$II=F;$$

$$III=F-L;$$

$$aVR=-\tfrac{1}{2}(L+F);$$

$$aVL=L-\tfrac{1}{2}F;$$

$$aVF=F-\tfrac{1}{2}L.$$

When determining heart axis, it is common to consider that a positive aVF points toward 90 degrees, and a negative aVF points toward −90 degrees. But, the formula for calculating aVF produces a negative value when F is positive and values of L are greater than two times F. This doesn't seem realistic and for our determinations of heart axis, the augmented values will not be used.

As noted above, the augmented leads (aVF, aVR, and aVL) will not be used because it seems they are likely to cause confusion. And since Lead III is derived from Lead I and Lead II, we will use Lead I and Lead II which are respectively equal to the voltage at Left Arm (L) and Left Leg (F) with the understanding that the Right Arm (R) voltage is defined as the common zero for all voltage measurements. This results in the Right Leg (RL) having a voltage that may be compared with the Left Leg (F) voltage, and for cases where the two voltages are sufficiently close to each other, it seems reasonable to define the voltage at 90 degrees to be equal to the voltage at F or equal to the average value of F and RL. This is further justified because, as noted above, reversal of the leg electrodes is often undetectable. This is also reason for using the Left Leg (F) or an average of F and RL rather than aVF for vector calculations.

Some rules and definitions are as follows:

1) A vector is defined by a magnitude equal to the voltage measured at an angle which defines the direction of the vector.

Figure 1:
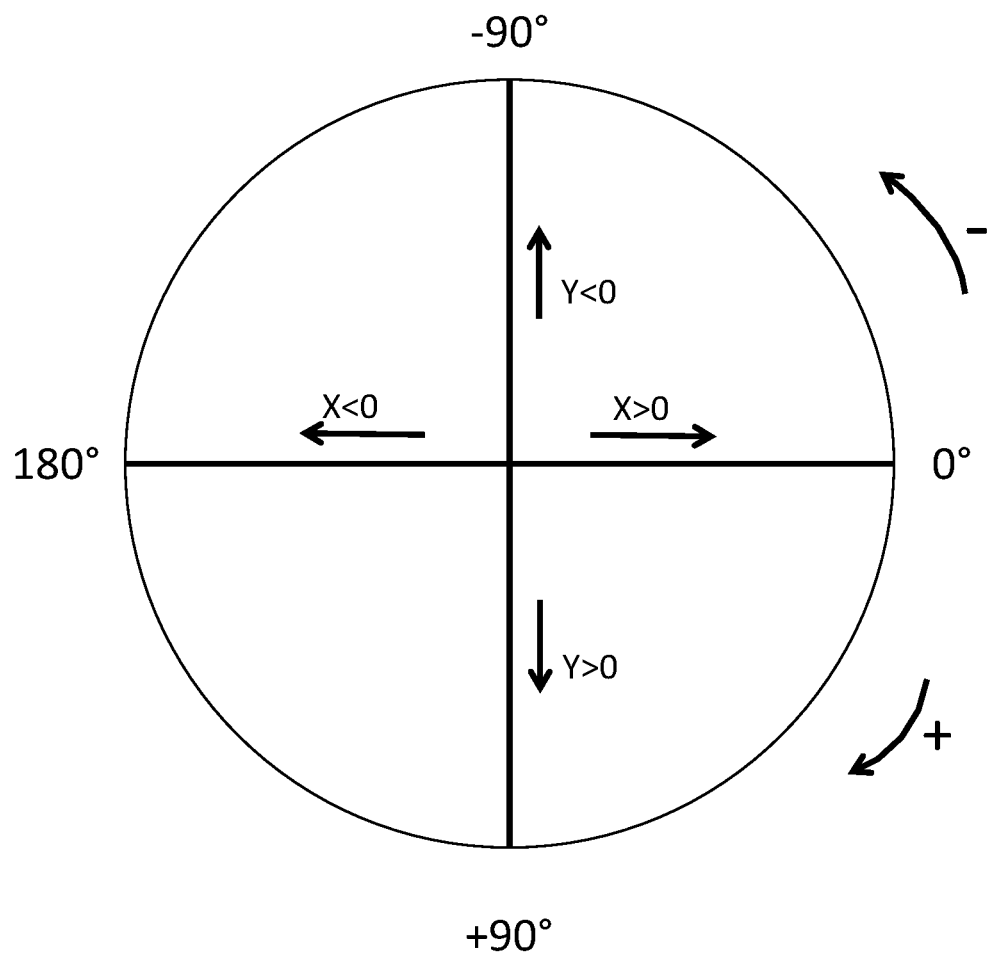
FIG. 1 illustrates the convention used to define vector angles A.
Figure 2:
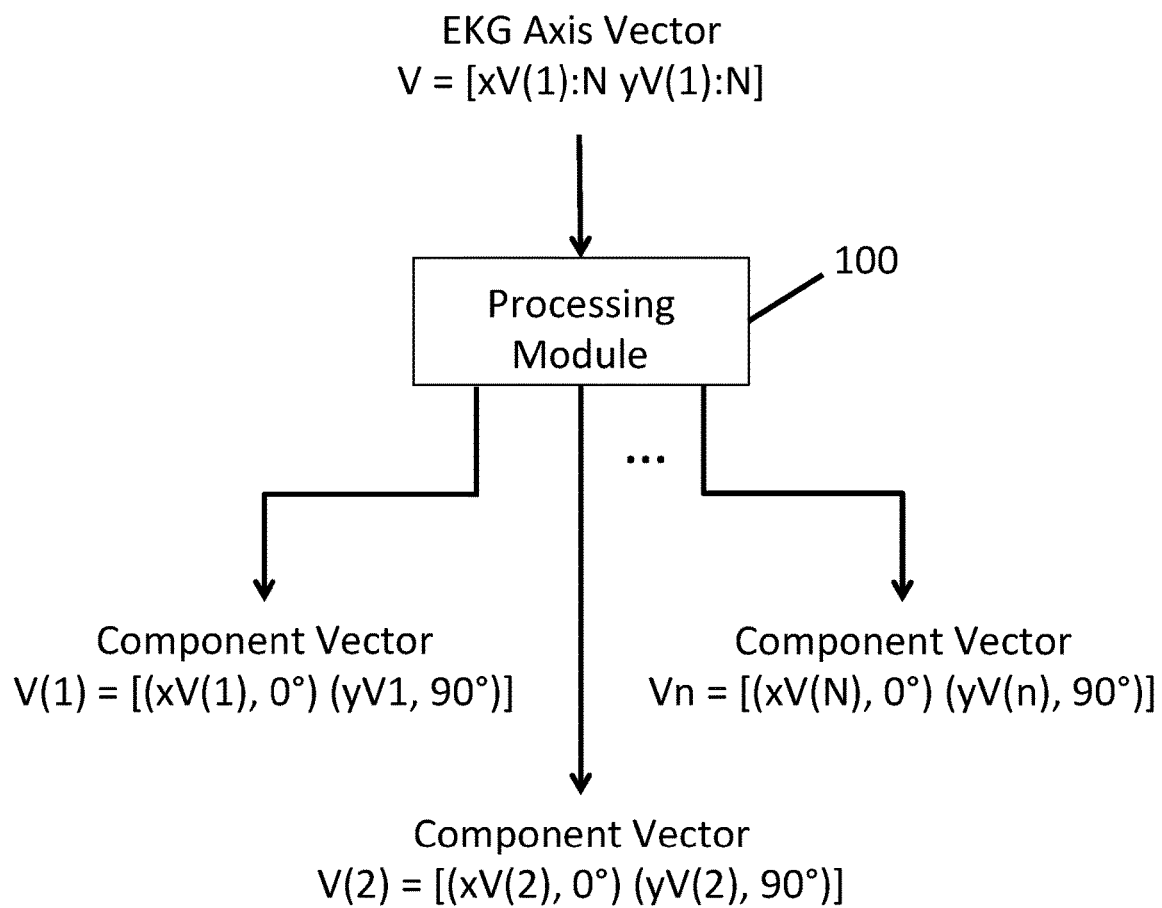
FIG. 2 is a functional diagram of an embodiment of a system of the present invention for modeling EKG signal sources.

2) Vectors are defined in a coordinate system with conventions common for EKG analysis but different than the system commonly used in trigonometry. In the EKG coordinate system, positive angles are measured clockwise from zero at the positive x-axis to 180 degrees at the negative x-axis. And negative angles are measured counter-clockwise from the positive x-axis to −180 degrees at the negative x-axis. (See FIG. 1.)

Determination of voltage polarity in several cases may be more important than voltage amplitude, particularly when the waveform has substantial positive and negative peaks.

One objective of the present invention is to determine the QRS axis angle A as a function of xV and yV, where xV=V(0) and yV=V(90)−V(−90).

Another objective is to determine V(0) and V(90) from V(A) for QRS axis at angle A.

A variety of methods are conventionally used for deriving the QRS axis from the amplitude of the QRS signal sensed at the Left Arm (L) and the Left Leg (F). One of the problems encountered in any method is the determination of the amplitude and polarity to be used when the QRS has significant positive and negative peaks. The system and method used herein will focus on receiving a QRS value and polarity from a trusted source. This means that only QRS and other reference complexes having a trusted amplitude including polarity will be used in vector computations.

Common rules for vector computations will be used with the understanding that a vector can be represented by one or more component parts. And to simplify the related trigonometry, it is common practice to represent vectors in three dimensions by x, y, and, z components. The focus herein will be limited to vectors in two dimensions, represented by x and y components, with the understanding that very similar processes are used for vectors in three dimensions.

In this description a vector is defined by a magnitude representing units of voltage and a direction angle in a coordinate system that combines rectangular and polar coordinates for convenient translation between the two types of coordinates. Vectors are commonly illustrated as an arrow having a direction angle and length proportional to the magnitude.

Vectors are represented in many different ways and there are several math programming products to work with them effectively, but it is difficult to identify vector parameters unambiguously with easily recognize characters without learning a new alphabet or language for each method. In this document vectors are expressed with English language characters and common punctuation marks, such as commas, periods, parenthesis, and square brackets. By default an upper case letter without a prefix is interpreted as a vector and vector mathematics is required when vectors are combined mathematically. Fortunately, for our purposes herein, only addition and subtracting are required, and we are careful to avoid adding or subtraction vectors unless they have the same direction angle, and in most cases the direction angles in degrees are zero plus or minus 90 or plus or minus 180. The following symbols and notation are used herein to describe vector relations:

| | |
|---|---|
| V | Represents a vector. |
| xV | Represents the x-component of vector V. |
| yV | Represents the y-component of vector V. |
| magV | Represents the magnitude of vector V. |
| A | Represents the direction angle of vector V. |
| aTan ( ) | Represents arc tangent. |
| sgn( ) | Represents the sign or polarity. |

A vector V is defined in several ways, each way providing exactly the same result:

$V=[xV\ yV]=[V(1)V(2) \ldots V(N)]=V(1:N)=\text{mag}V$ at direction angle $A$ $xV=[xV(1)xV(2) \ldots xV(N)]=$ Sum of $xV(1:N)$ $yV=[yV(1)yV(2) \ldots yV(N)]=$ Sum of $yV(1:N)$ $\text{mag}V=$ Square Root of $(xV^2+yV^2)$.

For $x>0, A=a\ \text{Tan}(yV/xV)$

For $x<0, A=a\ \text{Tan}(yV/xV)+\text{sgn}(yV)*180$

It is known that any vector can be represented by an infinite number of components and, while the number of components that combine to produce an EKG axis vector is very large, it is still finite. When approximating electrical activity of the heart it is useful to consider how to handle a very large but finite number of vector components that might combine to produce a resultant EKG axis vector. A system and method for providing and identifying such a large number of components is disclosed herein.

If we limit our vectors of interest to those having x-y components with integer values, we can uniquely define as many as we want in a finite set. For example consider a rectangle having a grid of vertical and horizontal lines on which a diagonal vector V defined by integer values for xV and yV is illustrated with its end points, head and tail, located on points where lines touch each other. Further consider that there are vertical lines indexed from zero to xV and there are horizontal lines indexed from zero to yV. Now to make a pair of vector components that define vector V with tail at (0, 0) and head at (xV, yV), we select a point to define the head of the first component and tail of the second component anywhere that is not outside the rectangle. This one point defines the end of the first component and the beginning of the second component. The number of component pairs we can define this way is calculated from the product of (xV+1) times (yV+1). If we choose not to count the pairs that begin or end at the two points representing the head and tail of the vector, we can eliminate two pairs.

The counting process is more complicated when each component set has more than two components. But, it is similar to the process disclosed previously for generating equal sum sequences for codes having a sum (S), a length (L), and a minimum value (minVal).

For example, for S=5, L=2 and minVal=1, an equal sum sequence beginning at 1 4 and ending at 4 1 has 4 members.

With minVal=0, the equal sum sequence beginning at 0 5 and ending 5 0 has 6 members. For S=5, L=3 and minVal=0, the equal sum sequence beginning at 0 0 5 and ending at 5 0 0 has members calculated from:

$$\frac{S+L-1}{S!*(L-1)!} = \frac{7!}{5!*2!} = 21$$

Figure 3A:
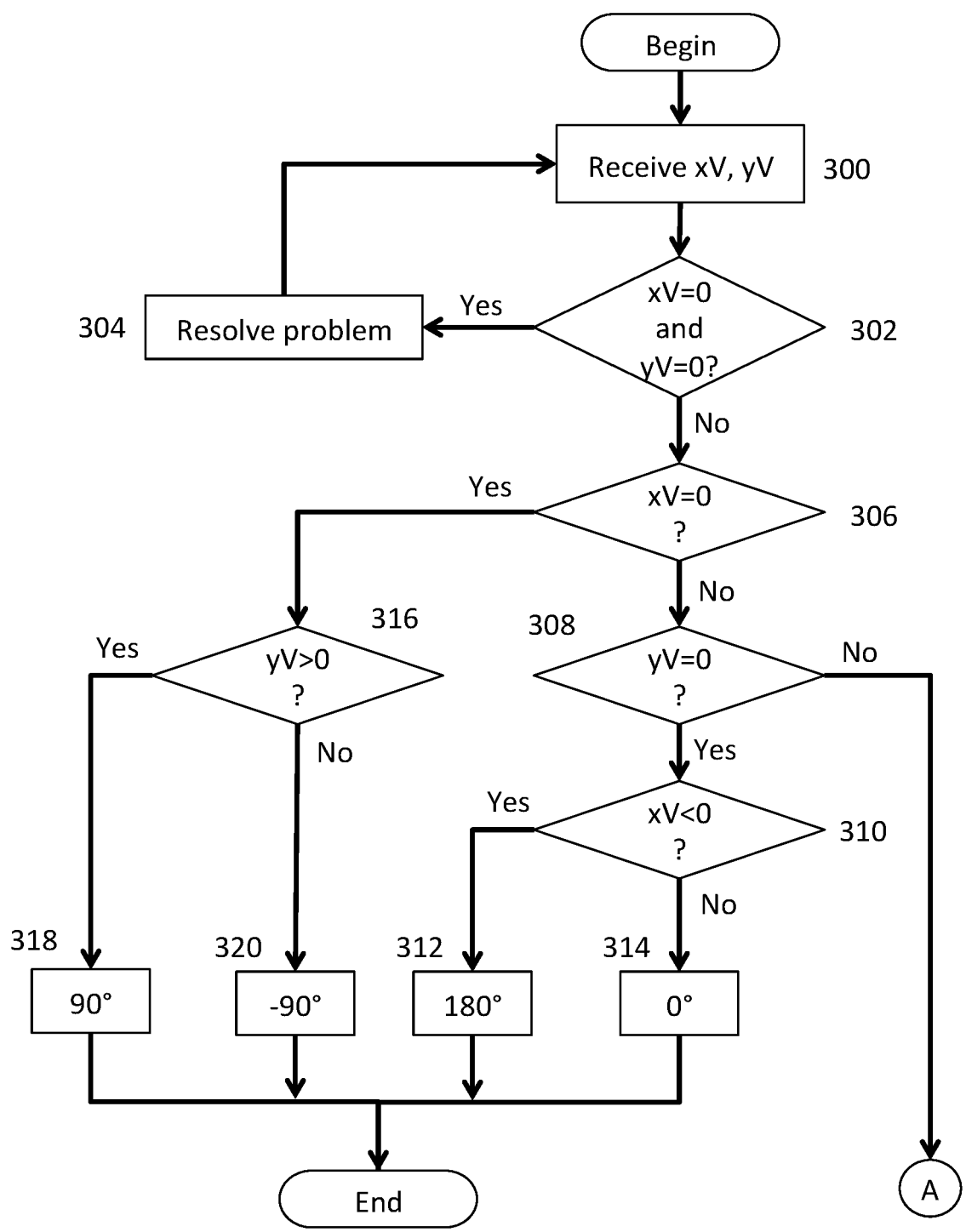
FIGS. 3A and 3B illustrate flowchart of a process for vector modeling EKG signals.
Figure 3B:
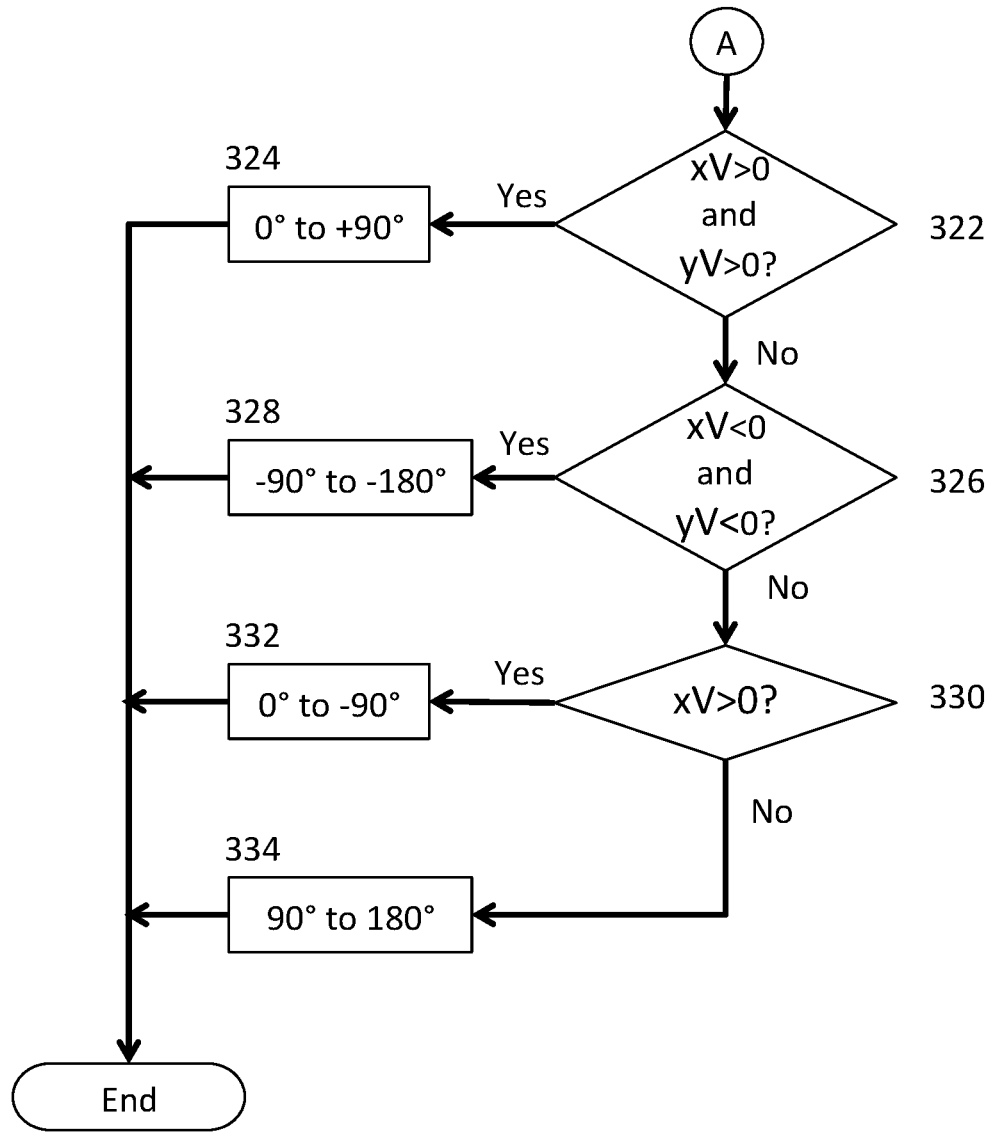

FIGS. 3A, 3B are a flowchart of a process for vector modeling of EKG signals. Signals xV and yV are received from the ECG electrodes (or simulated artificially by a signal generator) (step 300). If both xV and yV equal zero (step 302), that is an indication that no signals were received and steps should be taken to resolve the problem (step 304). If either or both xV and yV don't equal zero, a determination is made as to whether xV equals zero (step 306). If not, a determination is made as to whether yV equals zero (step 308). If, instead, yV equals zero, a determination is made as to whether xV is greater than zero (step 310). If so, the vector angle is 180° (step 312) and the process ends. If xV is not equal to zero, the vector angle is 0° (step 314) and the process ends.

Returning to the determination at step 306, if xV equals zero, a determination is made as to whether yV is greater than zero (step 316). If so, the vector angle is 90° (step 318) and the process ends. If not, the vector angle is –90° (step 320) and the process ends.

Returning to the determination at step 308, if yV is not zero, the process continues with a determination of whether xV and yV are both greater than zero (step 322, FIG. 3B). If so, the vector angle is between 0° and 90° (step 324) and the process ends. If not, a determination is made as to whether xV and yV are both less than zero (step 326). If so, the vector angle is between –90° and –180° (step 328) and the process ends. If not, a determination is made as to whether xV is greater than zero (step 330). If so, the vector angle is between 0° and –90° (step 332) and the process ends. If not, the vector angle is between 90° and 180° (step 334) and the process ends.

Thus, it may be determined on which coordinate axis or in which quadrant the EKG axis vector angle lies. The actual angle A for any quadrant may be calculated as a function of xV and yV.

Figure 4:
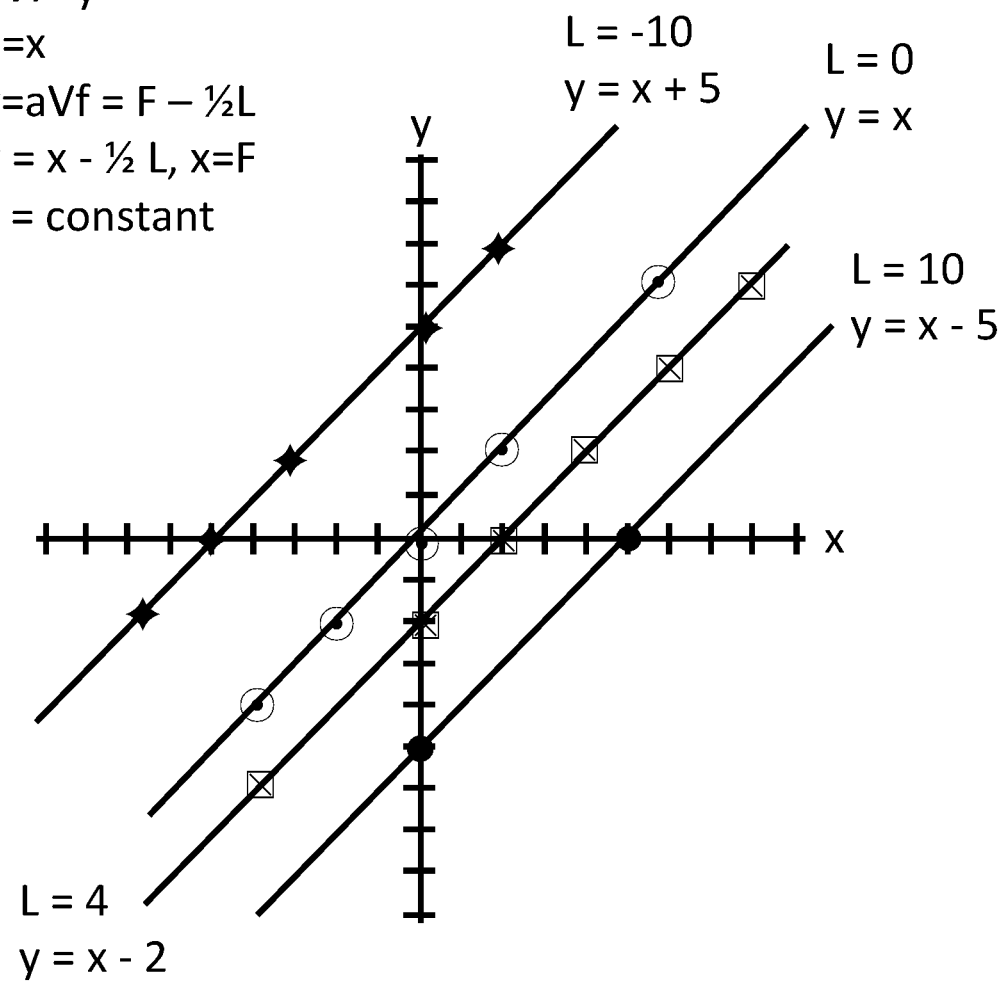
FIG. 4 is a plot of aVF=F−½L, for several values of constant L.
Figure 5:
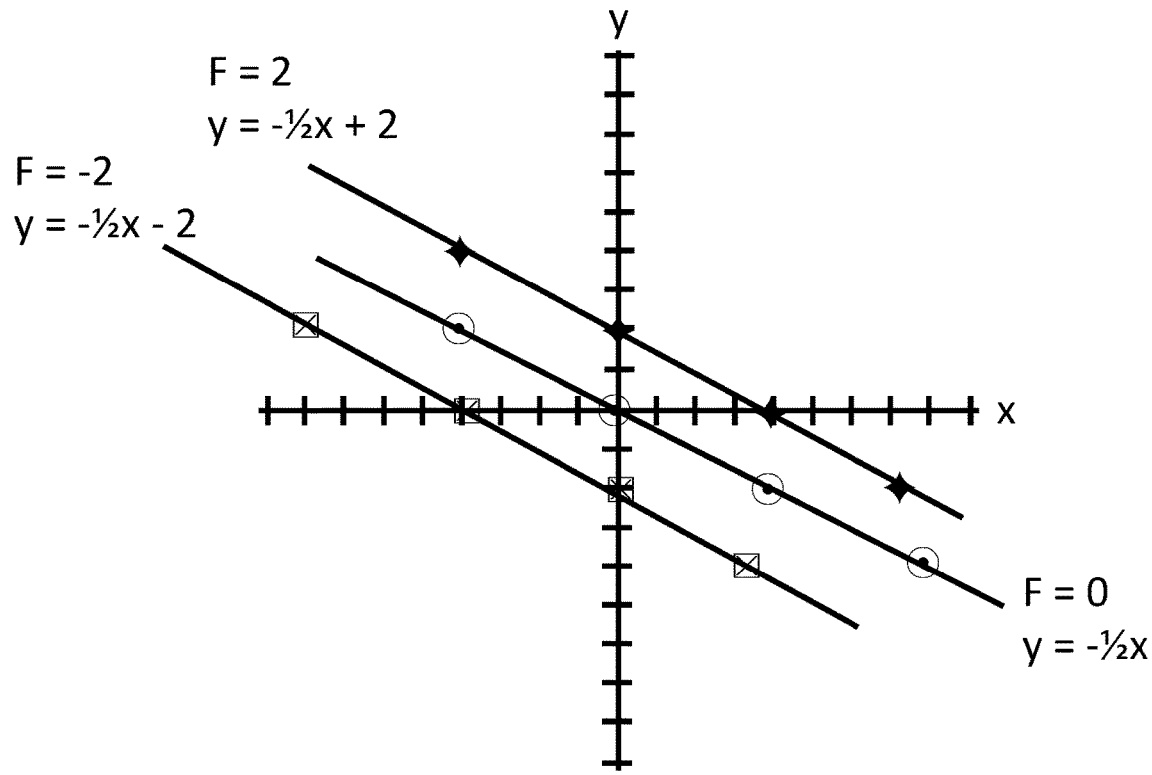
FIG. 5 is a plot of aVF=−½L+F, for several values of constant F.
Figure 6:
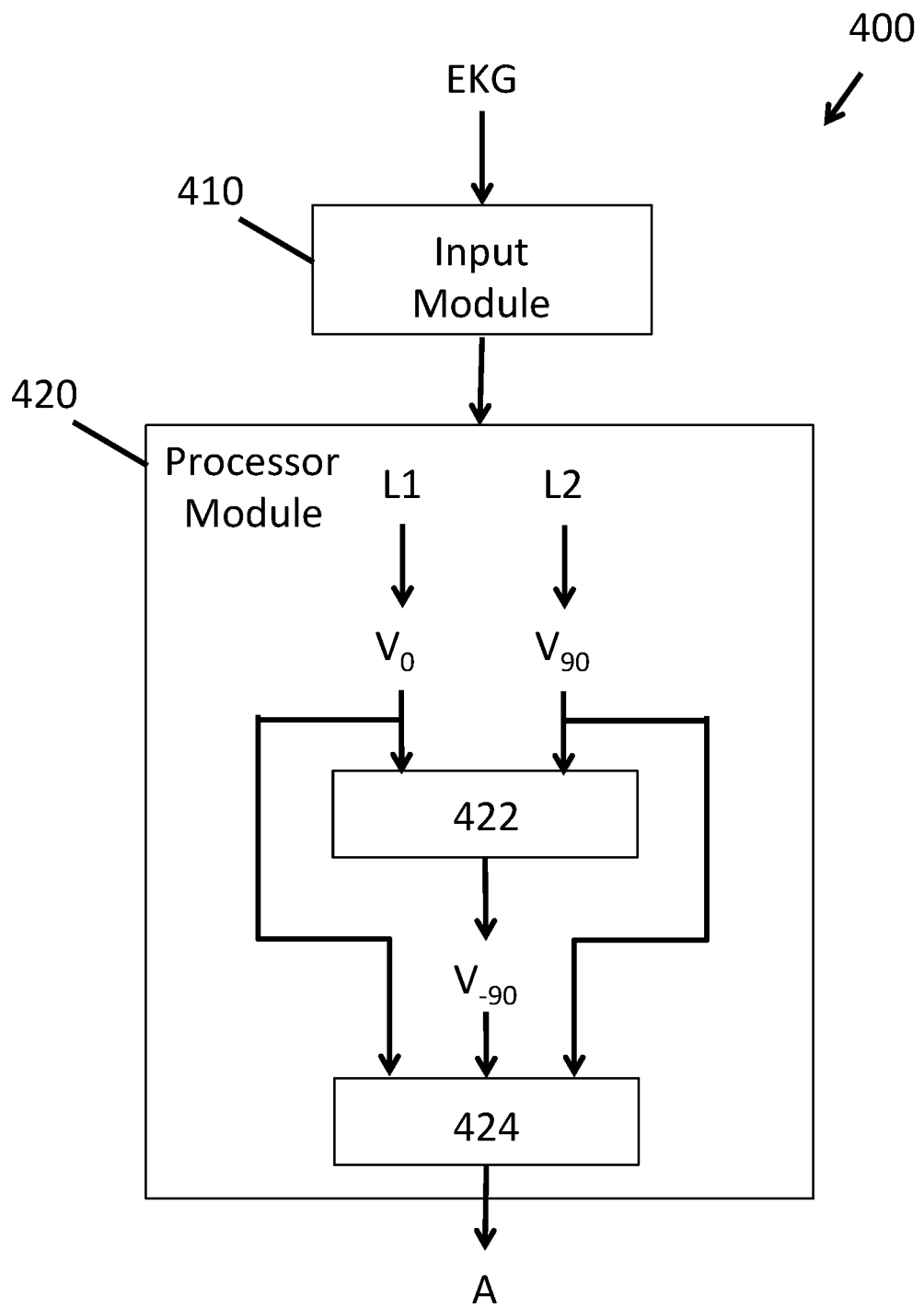
FIG. 6 illustrates a system for providing an EKG axis angle (A)

FIG. 4 is a plot of aVF=F–½L for several values of constant L and FIG. 5 is a plot of aVF=–½L+F for several values of constant F. The plots seem to demonstrate that one can't interpret aVF as if it is a physical position on the body FIG. 6 illustrates a system 400 for providing an EKG axis angle (A). The system 400 comprises an input module 410 to receive EKG signals representing Lead 1 and Lead 2 and a processing module 420 to provide a voltage V(0) from Lead 1 and a voltage V(90) from Lead 2, where V(0) represents a voltage at an angle of zero degrees and V(90) represents the voltage at an angle of 90 degrees in a model used to identify angular relationships between EKG leads. The processing module 420 is further configured to provide 422 a voltage V(–90) as a function of V(0) and V(90) and to calculate using 424 the axis angle A as a function of V(90), V(–90) and V(0).

Figure 7:
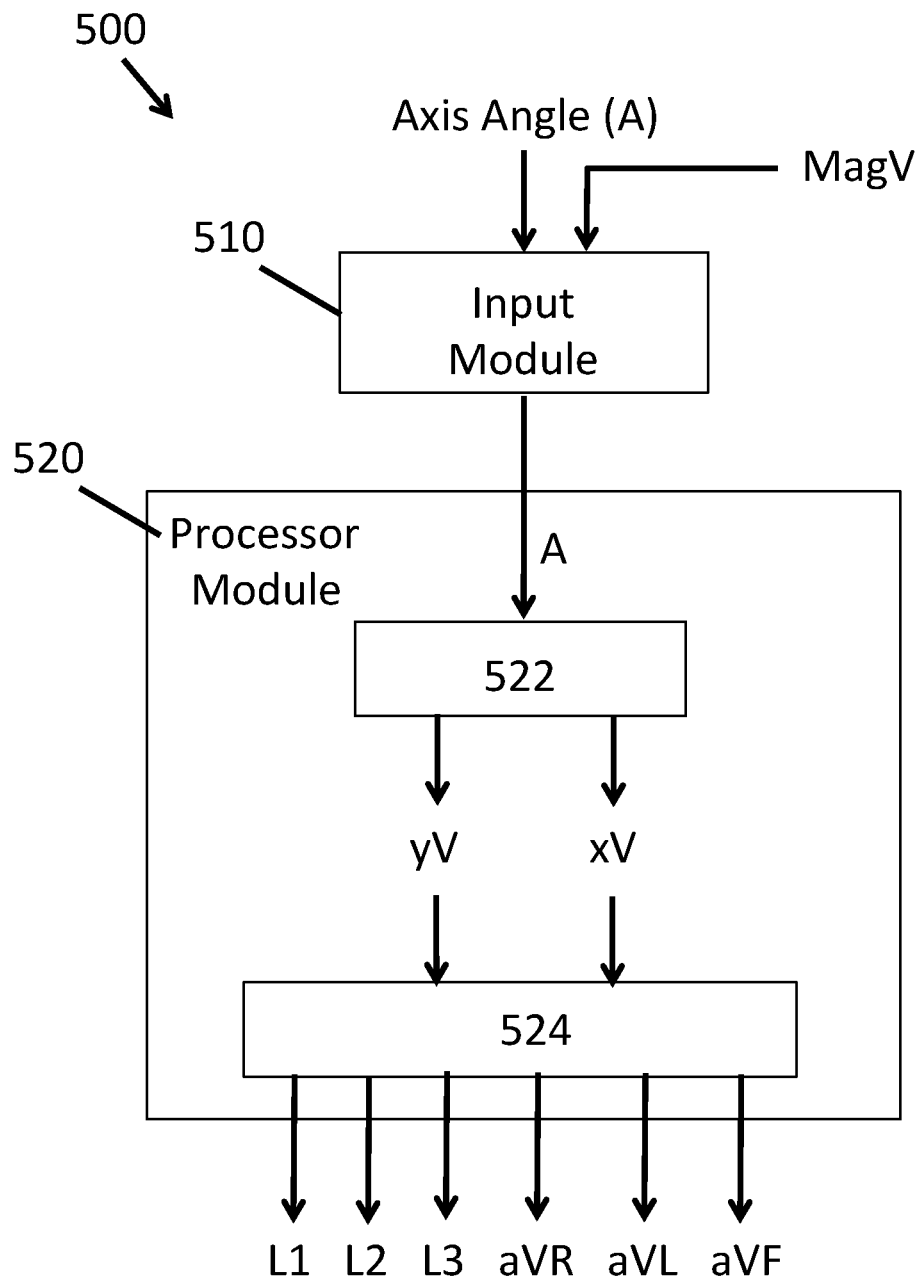
FIG. 7 illustrates a system for providing simulated EKG signals for Leads 1, 2, and 3, aVR, aVL, and aVF.

FIG. 7 illustrates a system 500 for providing simulated EKG signals for Leads 1, 2, and 3, aVR, aVL, and aVF. The system 500 comprises an input module 510 for receiving a value A representing an EKG axis angle and a processing module 520. The processing module is configured to provide from 522 a vertical component yV and a horizontal component xV for an axis vector defined by magV at angle A, where magV represents a user adjustable default voltage across the axis vector, and to provide from 524 simulated signals representing EKG signals for Leads 1, 2, 3, aVR, aVL, and aVF as a function of xV and yV.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A system for generating a sequence of electric signals represented by vector component sets, the system comprising:
   an input for receiving a representation of a vector V;
   a processor for providing xV and yV from the received vector V, such that V is represented by xV(1 ... M) and yV(1 ... M), where M is an integer greater than zero;
   a sequence generator for generating a sequence of x-components, where xV equals the sum of xV(1) through xV(M), and for generating a sequence of y-components, where yV equals the sum of yV(1) through yV(M); and
   an output for providing sets of values for xV and yV up to a maximum number of sets of values as a function of xV, yV, and M, whereby a sequence of vector component sets is generated.

2. The system of claim 1 wherein the received representation of vector V comprises the relation:
   V=magV at direction angle A, where:

$$magV = \sqrt{xV^2 + yV^2} \text{ ; and}$$
$$A = \arctan\left(\frac{yV}{xV}\right).$$

3. The system of claim 1 wherein the vector V is represented by vector components xV and yV.

4. The system of claim 1 wherein the maximum number of x-components is calculated from the relation:

$$\frac{(S - u*L + L - 1)!}{(S - u*L)! * (L - 1)!},$$

where:
   S=xV;
   L=number of members of xV; and
   u=a minimum value of a member of xV.

5. The system of claim 1 wherein the maximum number of x-components is calculated from the relation:

$$\frac{(S - 1)!}{(S - L)! * (L - 1)!},$$

where:
   S=xV; and
   L=number of members of xV.

6. The system of claim 1 wherein the processor provides integer values for xV, yV, and magV.

7. The system of claim 1 wherein the sequence generator provides a number of component sets less than three.

8. The system of claim 1 wherein the sequence generator provides a number of component sets greater than two.

9. A method for generating a sequence of electric signals represented by vector component sets, the method comprising:
   receiving a representation of a vector V;
   providing xV and yV from the received vector V, such that V is represented by xV(1 ... M) and yV(1 ... M), where M is an integer greater than zero;
   generating a sequence of x-components, where xV equals the sum of xV(1) through xV(M), and for generating a sequence of y-components, where yV equals the sum of yV1 through yV(N); and
   providing sets of values for xV and yV up to a maximum number of sets as a function of xV, yV, and M, whereby a sequence of vector component sets is generated.

10. The method of claim 9 wherein the received representation of vector V comprises the relation:
    V=magV at direction angle A, where:

$$magV = \sqrt{xV^2 + yV^2} \text{ ; and}$$
$$A = \arctan\left(\frac{yV}{xV}\right).$$

11. The method of claim 9 wherein the vector V is represented by vector components xV and yV.

12. The method of claim 9 wherein the maximum number of x-components is calculated from the relation:

$$\frac{(S - u*L + L - 1)!}{(S - u*L)! * (L - 1)!},$$

where:
   S=xV;
   L=number of members of xV; and
   u=a minimum value of a member of xV.

13. The method of claim 9 wherein the maximum number of x-components is calculated from the relation:

$$\frac{(S - 1)!}{(S - L)! * (L - 1)!},$$

where:
   S=xV; and
   L=number of members of xV.

14. The method of claim 9 wherein providing sets of values further comprises providing integer values of magV.

15. The method of claim 9 wherein M is an integer less than three.

16. The method of claim 9 wherein M is an integer greater than two.

17. A system for providing an electrocardiogram (EKG) axis angle (A), the system comprising:
   an input to receive EKG signals representing Lead 1 and Lead 2; and
   a processor to provide a voltage V(0) from Lead 1 and a voltage V(90) from Lead 2, where V(0) represents a voltage at an angle of zero degrees and V(90) represents the voltage at an angle of 90 degrees in a model used to identify angular relationships between EKG leads;

the processor configured to provide a voltage $V(-90)$ as a function of $V(0)$ and $V(90)$ and to provide the axis angle A as a function of $V(90)$, $V(-90)$ and $V(0)$.

18. A system for simulating electrocardiogram (EKG) signals for Leads 1, 2, and 3, aVR, aVL, and aVF, the system comprising:

an input for receiving a value A representing an EKG axis angle; and a processor configured to:

provide a vertical component yV and a horizontal component xV for an axis vector defined by magV at angle A, where magV represents a user adjustable default voltage across the axis vector; and provide simulated signals representing EKG signals for Leads 1, 2, 3, aVR, aVL, and aVF as a function of xV and yV.

19. The system of claim 17 wherein $V(0)$ is set equal to the voltage at Lead 1 and $V(90)$ is set equal to the voltage at Lead 2.

20. The system of claim 17 wherein $V(-90)$ is set equal to $V(0)$ minus 90 when both $V(0)$ and $V(90)$ are positive.

21. The system of claim 17 wherein $V(-90)$ is set equal to 90 when $V(0)$ is positive and $V(90)$ is negative.

22. The system of claim 18 wherein magV is set equal to 180 voltage units (vu).

23. The system of claim 22 wherein angle A is set between zero (0) and 90 degrees.

24. The system of claim 23 wherein Lead 1 is set equal to xV, which is equal to $V(0)$ where $V(0)=180-2*A$, and Lead 2 is set equal to $V(90)$, which is equal to $yV+V(-90)$ where $V(-90)=V(0)-90$.

25. A method for providing an electrocardiogram (EKG) axis angle (A), the method comprising:

receiving EKG signals representing Lead 1 and Lead 2;

providing a voltage $V(0)$ from Lead 1 and a voltage $V(90)$ from Lead 2, where $V(0)$ represents a voltage at an angle of zero degrees and $V(90)$ represents the voltage at an angle of 90 degrees in a model used to identify angular relationships between EKG leads;

providing a voltage $V(-90)$ as a function of $V(0)$ and $V(90)$; and calculating the axis angle A as a function of $V(90)$, $V(-90)$ and $V(0)$.

26. The method of claim 25 wherein $V(0)$ is set equal to the voltage at Lead 1 and $V(90)$ is set equal to the voltage at Lead 2.

27. The method of claim 25 wherein $V(-90)$ is set equal to $V(0)$ minus 90 when both $V(0)$ and $V(90)$ are positive.

28. The method of claim 25 wherein $V(-90)$ is set equal to 90 when $V(0)$ is positive and $V(90)$ is negative.

29. A method for simulating electrocardiogram (EKG) signals for Leads 1, 2, and 3, aVR, aVL, and aVF, the method comprising:

receiving a value A representing an EKG axis angle;

providing a vertical component yV and a horizontal component xV for an axis vector defined by magV at angle A, where magV represents a user adjustable default voltage across the axis vector; and providing simulated signals representing EKG signals for Leads 1, 2, 3, aVR, aVL, and aVF as a function of xV and yV.

30. The method of claim 29 wherein magV is set equal to 180 voltage units (vu).

31. The method of claim 30 wherein angle A is set between zero (0) and 90 degrees.

32. The method of claim 31 wherein Lead 1 is set equal to xV, which is equal to $V(0)$ where $V(0)=180-2*A$, and Lead 2 is set equal to $V(90)$, which is equal to $yV+V(-90)$ where $V(-90)=V(0)-90$.

* * * * *